United States Patent
Daltrozzo et al.

(10) Patent No.: US 6,552,199 B1
(45) Date of Patent: Apr. 22, 2003

(54) FLUORESCENCE DYES AND THEIR USE AS FLUORESCENCE MARKERS

(75) Inventors: Ewald Daltrozzo, Constance (DE); Alexander Reiss, Frickingen (DE)

(73) Assignee: Roche Diagnostics GmbH (DE)

( * ) Notice: Subject to any disclaimer, the term of this patent is extended or adjusted under 35 U.S.C. 154(b) by 0 days.

(21) Appl. No.: 09/568,679

(22) Filed: May 11, 2000

(30) Foreign Application Priority Data

May 20, 1999 (DE) .......................... 199 23 168

(51) Int. Cl.[7] .................... C07D 215/12; C07D 277/62; C07D 207/40; C07D 311/82
(52) U.S. Cl. .................... 546/174; 544/135; 546/198; 546/152; 548/156; 548/546; 548/547; 549/223
(58) Field of Search ................. 546/198, 174, 546/152; 544/135; 548/156, 546, 547; 549/223

(56) References Cited

U.S. PATENT DOCUMENTS

| 3,679,358 A | 7/1972 | Lohe et al. | 8/177 AB |
|---|---|---|---|
| 5,210,015 A | 5/1993 | Gelfand et al. | 435/6 |
| 5,847,162 A | 12/1998 | Lee et al. | 549/227 |
| 6,008,379 A | * 12/1999 | Benson | 549/224 |

FOREIGN PATENT DOCUMENTS

| CH | 12433/70 | 8/1970 | ............. D06P/3/76 |
|---|---|---|---|
| DE | 19521231 A1 | 12/1996 | ........... C09B/19/00 |
| EP | 0543333 A1 | 5/1993 | ........... C09B/11/24 |
| WO | WO88/04777 | 6/1988 | ......... G01N/33/533 |
| WO | WO99/16832 | 4/1999 | ........... C09B/11/08 |

OTHER PUBLICATIONS

Addendum "A Technique for Radiolabeling DNA Restriction Endonuclease Fragments to High Specific Activity" Analytical Biochemistry 137, 266–267 (1984).

Sudhir Agrawal, "Protocols for Oligonucleotides and Analogs" Methods in Molecular Biology 20 (Chapter 1 pp. 1–17, Chapter 3 pp. 33–61 and Chapter 4 pp. 63–80) 1993 Human Press, Inc.

Adolf Baeyer, "Ueber die Verbindungen der Phtalsaure mit den Phenolen" Justus Liebig's Annalen Der Chemie 183 Band. pp. 1–74.

B. Wieb Van Der Meer George Coker, et al. "Resonance Energy Transfer" VCH Chapter 7 Data pp. 133–173.

Jerry March "Advanced Organic Chemistry" Reactions, Mechanisms, and Structure, Fourth Edition pp. 417–425, A Wiley–Interscience Publication.

Paidi Yella Reddy et al. "Efficient Synthesis of Fluorophor–Linked Malemide Derivatives" Jul. 1998 Synthesis pp. 999–1002.

Reddy, et al. "Efficient Synthesis of Fluorophore–Linked Malemide Derivatives" Sci Finder Jul. 27, 2000 (4pgs).

Peter W. J. Rigby et al., "Labeling Deoxyribonucleic Acid to High Specific Activity in Vitro by Nick Translation with DNA Polymerase I" J. Mol. Biol. (1977) 113, 237–251.

Dana B. Shealy, et al., "Synthesis, Chromatographic Separation, and Characterization of Near–Infrared–Labeled DNA Oligomers for Use in DNA Sequencing" Anal. Chem. 1995, 67, 247–251.

* cited by examiner

*Primary Examiner*—Evelyn Mei Huang
(74) *Attorney, Agent, or Firm*—Marilyn L. Amick; Roche Diagnostics Corporation

(57) ABSTRACT

The subject matter of the invention are new xanthene derivatives of the formula I,

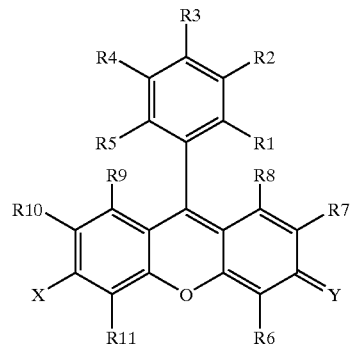

wherein R1, R2, R3, R4, R5, R6, R7, R8, R9, R10, R11, and X, Y, are as defined herein. The compounds according to the invention provide molecules that are—due to their spectral properties (absorption maxima in the range of approx. 650 nm and above as well as emission maxima above 670 nm)—very suitable for the use as dyes and in particular as fluorescence dyes. The compounds of the formula I according to the invention are used for the production of fluorescence conjugates, for their application in immunoassays, for DNA analytics, for in-vivo diagnostics or as a laser dye.

19 Claims, No Drawings

FLUORESCENCE DYES AND THEIR USE AS FLUORESCENCE MARKERS

The claimed invention concerns the production of new fluorescence dyes with an absorption region above 650 nm, their use as biomolecule markers, and the use of the marker-biomolecule conjugates in diagnostic systems.

To perform immunological assays and in DNA analytics markers or labels allowing the quantification of the analyte after the completion of an analyte-specific reaction are needed.

Recently, fluorescence labels in particular have become generally accepted due to their high sensitivity degree. The labeling of an antibody or an oligonucleotide with fluorescence dyes enables thus a direct quantification.

Widespread fluorescence dyes are for example FITC (fluorescein isothiocyanate), FLUOS (fluorescein N-hydroxysuccinimide ester), resorufin and rhodamine labels which do, however, need a relatively high light source for their excitation, such as an argon laser.

The quick development of inexpensive laser diodes with an emission range from 630–780 nm, and which are very appropriate for miniature system arrangements, makes dyes absorbing within these wave length ranges so desirable.

In EP-A-0 543 333 pentacyclic rhodamine dyes suitable for being used as labels are described. The main absorption range of such dyes is $\leq 660$ nm.

In WO 88/047 77 phthalocyanine dyes are described that have more than one functional group so that in the case of conjugation, e.g. with antibodies, they result in cross-linking and product mixtures requiring a high degree of purification.

In DE 195 21 231 new oxazine dyes with an absorption maximum of up to 700 nm and their use as fluorescence markers are described.

The object of the present invention is to provide dyes suitable for coupling with biological molecules having a high quantum yield, absorbing within a spectral region above 650 nm, and exhibiting an unspecific binding as low as possible to biological compounds or to solid phases.

This object is achieved by the invention as characterized in the claims.

The subject matter of the invention are new xanthene derivatives of the general formula I,

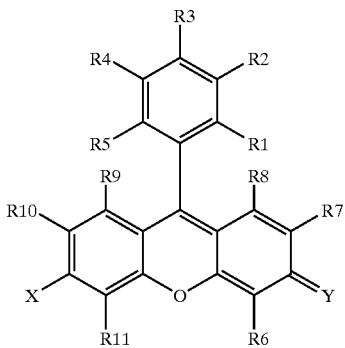

wherein R1,R2, R3, R4, R5 can be—independently of each other (or each)—hydrogen, alkyl, aryl, heteroaryl, alkoxy, cyano, hydroxy, halogen, isocyanate, isothiocyanate or carboxyl, sulfonyl and, respectively derivatives thereof such as alkoxycarbonyl, aryloxycarbonyl, active ester, acid halogenides, mixed anhydrides or unsubstituted or substituted amino residues, especially ω-amino alcohols, ω-aminocarboxylic acids or ω-aminohalogen alkanes.

It has been proven to be advantageous to have at least one residue of the group R1,R2, R3, R4, R5 representing a halogen, in particular fluorine or chlorine and at least one residue of the group R1,R2, R3, R4, R5 representing a functional group, preferably an acidic group, particularly preferably a carboxylic acid or a derivative thereof. The residues R6, R7, R8, R9, R10, R11 are—independently of each other—hydrogen, alkyl-, substituted alkyl residues or a halogenide, particularly preferred are hydrogens or alkyl residues with 1-10 C-atoms, or sulfoalkyl residues, especially sulfomethyl residues or chlorine and fluorine residues.

At least one of the residues X or Y is electrophilic. Preferred electrophilic residues are C-nucleophiles from activated methyl aromatics or heteroaromatics like, e.g. heteroarylidenecyanomethine of the type 2-benzthiazolylidenecyanomethine or 2- or 4-quinolinylidenecyanomethine or malonic acid derivates, such as 2-propyldinitril residues or cyanoacetic acid ester.

At least X or Y is such a residue, or X and Y are such residues. These residues X and Y can be identical or different.

Moreover, X can also be amine- or a substituted amine residues, particularly preferred are alkyl-substituted or cyclic amines where Y is selected from the series of the electrophilic residues (in particular heteroarylidenecyanomethine residues or malonic acid derivatives), as they are described above.

The compounds according to the invention provide molecules which are due to their spectral properties (absorption maxima within the region of approx. 650 nm and above as well as emission maxima above 670 nm) very suitable as dyes and particularly as fluorescence dyes. Particularly preferred are absorption maxima above 700 nm. At the same time the spectral properties of the molecules can be changed by the fact that the identity, number and position of the residues with respect to R1, R2, R3, R4, R5, R6, R7, R8, R9, R10, R11 is changed. This way, fluorescence dyes can be produced with almost any absorption and emission maximum above 650 nm. A subject matter of the invention therefore also is the use of the xanthene derivatives according to the invention as a fluorescence dye or as a laser dye.

Among the compounds according to the invention of the general formula I at least one of the residues R1, R2, R3, R4, R5 preferably is present in the form of an activated group suitable for coupling or in the form of a group which can be activated for coupling. Such an activated group is particularly derived from a carboxylic-acid or sulfonic acid group which can be activated, and can for example be an acid ester, an acid anhydride, an acid halogenide, preferably bromide, in particular chloride or an N-hydroxysuccinimide ester or a ω-alkylhalogenide. Furthermore, such an activated group can for example also be phosphoramidites.

The table below gives some examples of activated groups suitable for coupling. The expert knows more of such groups from the field of conjugate synthesis.

TABLE 1

| Activated group | Coupling with | Product |
| --- | --- | --- |
| NHS-ester | Amines | Amide |
| Isothiocyanate | Amines | Thiourea |
| (mixed) Anhydride | Amines | Amides |
| Maleinmide | Thiol | Thioether |
| Thiol | Maleinmide | Thioether |
| Haloacetyl | Thiol | Thioder |
| Hydrazines | Aldehyde | Hydrazones |
| Amines | Aldehyde | Amines (after reduction) |
| Amines | Reactive carboxylic acid | Amides |
| Phosphoramidites | Protected nucleotides | Labeled oligonucleotides |

For the production of conjugates containing the xanthene derivates according to the invention activated derivatives which are for example suitable for biomolecule labeling or labeling of other analytic reagents can be synthesized. The production of the activated derivatives requires at least one of the groups capable of being activated and located at the residues R1, R2, R3, R4, R5 and, respectively, X or Y, where activation is performed according to standard protocols known to the expert. Generally, activation is carried out with at least one hydroxyl group, amino-, sulfo- or carboxyl group of R1, R2, R3, R4 or R5.

Depending on the subsequent application different reactive groups can be introduced. Phosphoramidites and H-phosphonates can for example be derived from a hydroxyl group. The production of xanthene phosphoramidites and, respectively. H-phosphonates is thus generally performed according to hitherto known protocols (Methods in Mol. Biol. Vol 20. "Protocols for Oligonucleotides and Analogs, Synthesis and Properties". S. Agrawal Hrsg., Humana Press Totowa, N.J.).

N-hydroxy-succininimide (NHS)-esters are however generally derived from a carboxyl group, maleinimides from an amino group (P. Y. Reddy, Synthesis(1998) 999) or by extension of an activated carboxylic acid with the corresponding ω-aminoalkylmaleinimide.

The production of NHS-esters is preferably performed according to the method described in EP 0 543 333, where the free carboxylic acid is admixed with NHS in the presence of a condensation reagent such as for example DCC or MEI. The production of xanthene isothiocyanates is preferably carried out by the reaction of amino groups with thiophosgene (Advanced Organic Chemistry, Mc Graw Hill, $2^{nd}$edition. p. 383, 1997).

The subject matter of the invention are therefore also activated derivatives of the xanthenes according to the invention. The reactive groups of the activated derivatives are preferably phosphoramidite, N-hydroxy-succininimide (NHS)-ester, maleinimide-alkylamide, H-phosphonate or isothiocyanate or ω-alkylhalogenides.

A further subject matter of the invention are conjugates obtainable by the binding of xanthene compounds according to the invention or activated derivatives thereof. Such conjugates are thus composed of at least two components, with one component representing a xanthene derivative according to the invention. Starting from the activated derivatives the production of the conjugates is carried out according to standard protocols. The appropriate conjugation methods to be applied are known to the expert.

The conjugates according to the invention can be used for analytic purposes as soon as a second component of the conjugate can bind to a binding partner to be analysed and the built complex can be identified by the detection of the fluorescence emitted by the built complex after excitation with light of an appropriate absorption wave length.

Due to the absorption in the NIR the compounds according to the invention are also suitable for the in vivo use. For this, water soluble derivatives of the dyes according to the invention and conjugates thereof are applied together with biomolecules. The in-vivo measurements are carried out by measuring the fluorescence or the absorption.

The use of the conjugates according to the invention is particularly suitable for diagnostic analyses or for analyses of medical or biological material. A subject matter of the invention are therefore particularly those conjugates capable of interacting with a biomolecule. These are conjugates that in general also contain one or several biomolecules as a further component.

These biomolecules contained in the conjugates can for example be single- or double-stranded nucleic acids such as DNA, RNA or triplex structures or nucleic acid analogs such as PNA, oligonucleotides as well as oligonucleotide derivatives but also single nucleotides, nucleotide derivatives, nucleotide analogs or nucleoside triphosphates. Labeling of such molecules takes place at the 5'-position, preferably by an NHS ester or a phosphoramidite, at the 3'-position however preferably via a dye-substituted carrier material like for example CPG. Labeling of other places such as, e.g. nucleic bases is preferably carried out by an NHS ester, too.

In the case of labeling of proteins, protein complexes, antibodies or amino acids conjugation is preferably performed by an NHS ester, m-maleinimides or an isothiocyanate or ω-alkylhalogenides. Examples of further conjugate components are vitamins, steroid hormones, lipid molecules as well as haptens. Moreover, more complex biological structures such as membrane fractions or whole cells can also be labeled.

A particular embodiment of the conjugates according to the invention are oligonucleotides conjugated with a xanthene derivative according to the invention. Oligonucleotides marked this way can be used for hitherto known methods of detection and analysis of nucleic acids, for example by in situ hybridization (Meyne and Myzis, Methods Mol. Biol. 33. 63–74, 1994) or also as primers in different sequencing methods (Sheealy et al., Anal. Chem. 67, 247–251, 1995).

Besides chemicosynthetic labeling of nucleic acids ribonucleoside triphosphates and, respectively, desoxyribonucleoside triphosphates marked with xanthene dyes according to the invention can be inserted as substrates for polymerases in nucleic acids by different enzymatic reactions. For DNA this is achieved with DNA polymerases for example by applying the Nick Translation method (Rigby et al., J. Mol. Biol. 113, p. 237, 1977) or by "Random Primed Labeling" (Feinberg and Vogelstein. Anal. Biochem. 137. p. 266, 1984). In the case of RNA this is for example achieved with T3, T7 or SP6 RNA-polymerases by means of transcription. A further method of nucleic acid marking is possible by the so-called 3'-tailing-reaction using the terminal transferase.

A further subject matter of the invention thus also is the use of conjugates according to the invention for marking of nucleic acids by chemical or enzymatic methods as well as the use of hybridization probes labeled according to the invention for the detection and analysis of nucleic acids.

For an analytic assay the xanthene derivative according to the invention is first excited with light of an appropriate wave length like for example a laser, laser diodes or LEDs. Depending on the analyte the fluorescence detection is performed by means of measuring methods known to the expert. These are for example fluorescence microscopy for in-situ methods or the detection of the emitted radiation by appropriate photo diodes.

Besides the direct excitation of the dye according to the invention using radiation energy of a suitable wave length excitation can also be achieved by the so-called fluorescence-resonance-energy transfer. With this principle a second fluorescence dye is excited with light of an appropriate wave length. Due to the local proximity of the two dyes a nonradiative energy transfer to the xanthene derivative according to the invention takes place subsequently (Van der Meer et al., Resonance Energy Transfer, VCH, 1994). The detection of the light emitted by this molecule at a certain wave length can be used preferably for the quantitative determination of the analyte. A subject matter of the invention therefore also is the use of a xanthene derivative according to the invention or of the corresponding conjugate as a component of a fluorescence-resonance-energy-transfer system.

The compounds according to the invention are preferably applied as resonance-energy acceptors. Preferred resonance-energy donors for all compounds according to the invention are fluorescence dye conjugates suitable for spectral analysis. A subject matter of the invention therefore also is the use of xanthene derivatives according to the intention or of the corresponding conjugates together with appropriate fluorescence-resonance-donor conjugates as a fluorescence-resonance-energy acceptor in a fluorescnce-resonance-energy-transfer system.

For the quantitative detection of nucleic acids hybridization probes marked with fluorescence dyes such as oligonucleotides are suitable, which can be detected by the principle of the fluorescence-resonance-electron transfer (FRET). In the case of oligonucleotides the terminal position 5' can for example be marked with one dye component of the FRET system and the 3' terminal position with the remaining dye component of the FRET system. The oligonucleotides can in this case also be marked within the sequence.

In a special embodiment such an oligonucleotide marked with 2 dyes is used during the nucleic acid amplification for the detection of the resulting products where the emission of the fluorescence-resonance-energy donor is determined. If the oligonucleotide is not bound to the target no donor fluorescence is measurable due to the nonradiative energy transfer. If however the oligonucleotide binds to the target DNA the two dye components are locally separated due to exonuclease activities of the DNA polymerase used so that a certain fluorescence degree of the FRET donor becomes measurable (U.S. Pat. No. 5,210,015).

In other preferred embodiments the different dyes are located at 2 different hybridization probes which can hybridize within local proximity to the target nucleic acid. These probes can for example be two oligonucleotide probes hybridizing to the same strand of the target nucleic acid, with the one dye at the 3' terminal nucleotide of the first probe and the other dye at the 5' terminal nucleotide of the second probe so that the distance between the two only consists of a small number of nucleotides, i.e. a number between 0 and 30. When using fluorescein combined with a xanthene derivative according to the invention distances of 0–15, particularly of 1–5 nucleotides and in many cases of only 1 nucleotide have proven to be advantageous. If the nucleotide distances between the dye components are kept probes not being conjugated with the dye at the terminal end but internally can also be used. In the case of double-stranded target-nucleic acids probes that bind to different strands of the target can also be used as far as there is a certain nucleotide distance of 0 to 30 nucleotides between the tho dye components.

A further subject matter of the invention thus is the use of a conjugate according to the invention consisting of an oligonucleotide and a xanthene derivative according to the invention for the analysis of nucleic acids where a further conjugate consisting of a second oligonucleotide and a further appropriate fluorescence dye is used and where after excitation of a dye preferably coupled to the second oligonucleotide a fluorescence-resonance-energy transfer can take place. Oligonucleotide combinations are in the following called "FRET pairs" and labeled as such.

It has been proven to be particularly advantageous to use such FRET pairs for the detection of amplification products during or after a polymerase chain reaction. A further subject matter of the invention is therefore the use of a conjugate according to the invention as a component of a FRET pair for the detection of reaction products of a nucleic acid amplification reaction. In a special test procedure one of the two amplification primers can at the same time be marked with one of the two dyes used and thus provide one of the two components of the FRET.

The use of suitable FRET pairs for the detection of the amplification products allows a so-called "Real-Time Monitoring" of PCR-reactions with determination of the data necessary for the amplification product generation depending on the number of reaction cycles primed. This is generally achieved by the fact that due to the reaction and temperature conditions during the annealing period needed for the amplification primers the oligonucleotides of the FRET pair also hybridize to the target nucleic acid and that with an appropriate excitation a measurable fluorescence signal is emitted. With the data obtained the amount of the target nucleic acid originally applied can be determined by quantitative analysis. Therefore these embodiments are particularly important for quantitative RT-PCR experiments in which RNA concentrations of a biological sample are quantified. A subject matter of the invention therefore also is the use of conjugates according to the invention as a component of a FRET pair for the detection of reaction products of a nucleic acid amplification reaction where the reaction product is detected in each cycle. Additionally, a subject matter of the invention is the use of conjugates according to the invention as a component of a FRET pair for the performance of a quantitative determination of the nucleic acid to be amplified.

In a different embodiment the detection of the amplification product takes place after completion of the amplification reaction with continuous temperature increasing in the course of a fusion curve analysis after hybridization of the FRET pair to the target nucleic acid to b e detected. Simultaneously, the fluorescence emitted depending on the temperature is determined. This enables the detection of sequences that—due to certain mismatches—hybridize less stringently with the FRET pair used. The fusion points determined this way can be used for the detection of point mutations or other polymorphisms. A subject matter of the intention therefore also is the use of conjugates according to the invention as a component of a FRET pair for the determination of fusion curves, in particular during the identification of polymorphisms and point mutations.

Such fluorescence-resonance-energy transfer processes can in general be used for the determination of molecule—molecule interactions such as e.g. protein—protein interactions or antigen-antibody reactions. A particular advantage is achieved when the reaction takes place under homogeneous conditions.

As a counterion each cation suitable for charge neutralization and compatible with the present anionic basic structure depending on the pH can be used.

The synthesis of the formula I compounds according to the invention actually represents the substitution of nucleofuge groups in 3',6'-positions of xanthenes or fluorans by C-nucleophiles, obtainable from CH-acidic base compounds. As nucleofuge groups the halogens (fluorine, chlorine, bromine. iodine), $SO_2R$—or $SO_3R$—groups (R=alkyl, aryl), phosphites etc. can be used, as C-nucleophiles the derivatives (anions) of CH-acidic compounds obtainable from bases, such as methylaromatics and, respectively, methylheteroaromatics activated by electrophilic substituents or malonic acid derivatives can be used. Preferably, 36'-dichlorofluorans, accessible from 3',6'-dihydroxyfluorans with $POCl_3/PCl_5$ according to the literature (A.v. Bayer, Liebigs Ann. 183(1876)18), are admixed with the derivatives of CH-acidic compounds obtainable with LDA (litiumdiisopropylamide).

The starting compounds are preferably selected in a way that the synthesis product contains a group suitable for activation. Such groups are activated according to known methods to obtain groups suitable for subsequent coupling with reactive groups of biologically active molecules to build biomolecule-dye conjugates. Between the activated groups and the biologically active molecules linkers can be inserted.

Linkers are used for variation of the distance between the dyes according to the invention and the biomolecules. Aminocaproic acid can for example be inserted in carboxylic acid for reasons of extension. This can also involve a change in functionality like for example by the reaction of the carboxylic acid with a maleinimidoalkylamine. Moreover, linker charges can effect the solubility of the dye. Aminoacids with charge carriers such as lysin or glutamic acid are particularly suitable for this effect.

With the compounds according to the invention new compounds are provided that are—due to their spectroscopic properties (absorption maximum above 650 nm)—very appropriate as absorption dyes suitable for coupling, particularly as fluorescence dyes for the use in hapten-, antibody-, protein conjugates, and very suitable for polynucleotide marking and latice dyeing (fluorescence latices).

Dyes of the xanthene derivatives according to the invention are especially suitable for insertion in latices if they are soluble in organic, non water-miscible solvents and insertable in latices by a swelling procedure. Such fluorescent latices of a diameter of approx. 50 nm up to several μm can be loaded by means of different coating methods, e.g. with proteins, haptens or nucleic acids.

Dye mixtures with at least one dye according to the invention, so that a resonance-energy transfer can take place are also suitable.

Particles with the same absorption length and differing emission wave lengths are appropriate for multiparameter analyses, i.e. for the determination of different analytes in a sample. For the use in hapten- antibody- protein- or polynucleotide conjugates it is advantageous to have water-soluble dyes. For this purpose compounds of the general formula I in which R1, R2, R3, R4, R5, R6, R7, R8, R9, R10, R11 are as hydrophilic as possible are preferably used. These compounds preferably are substituted products containing, e.g. carboxylic or and sulfonic acid groups. Conjugate coupling takes place via at least one of the activated substituents of the residues R1, R2, R3, R4, or R5 and particularly via a hydroxyesuccinimide group.

Conjugates of the fluorescence dyes with haptens such as e.g. theophylline, digoxine, T3, T4 or proteins such as antibodies are for example suitable for use in diagnostic systems, in particular for fluorescence immunoassays fluorescence polarization immunoassays.

A further subject matter of the present invention is a procedure for the determination of a first, immunologically connectable substance wherein a conjugate of a compound according to the invention is used together with a second (immunologically) connectable substance which can be similar or different with regard to the first substance, and the absorption-, fluorescence- or fluorescence-polarization change of the compound according to the invention caused by an (immunological) binding reaction specific for the first substance is determined as a measure of the amount of the substance to be analyzed and contained in the sample.

A further subject matter of the invention is the use of the conjugates according to the invention in immunoassays.

By means of a series of concrete examples given in the following the synthesis of the xanthene derivatives is shown.

If the basic structure is a fluoran the carboxylic function in position R1 of the formula I is a lactone ring. The remaining residues R2 to R11 correspond to the definitions depicted in claim 1. As it is known to the expert the fluoran form characterized by the closed lactone ring at R1 can be transformed to the xanthene form by ring opening. The invention includes both basic structures.

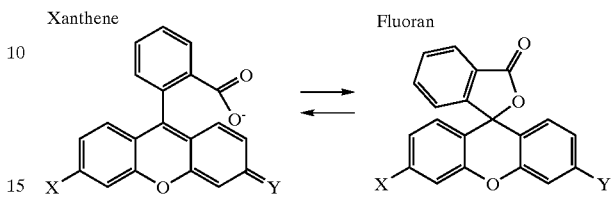

Xanthene                    Fluoran

For the synthesis of a series of substance classes (2, 4, 6, 8) the following general working conditions must be met and are occasionally also applicable to the synthesis of other substance classes. (A) Under protective gas conditions a 0.1 M solution of LDA (lithiumdiisopropylamide) is prepared from diisopropylamnine and n-butyllithium in dioxane. The solution is cooled down to approx. 7° C. and an equimolar amount of a CH-acidic component is added. This mixture is called LDA-CH acid. To this mixture the 3',6'nucleofuge-substituted fluoran derivative (0.4 mol per mol LDA) is added and the resulting compound is heated for six hours under reflux. The following procedure steps are carried out according to the reprocessing method 1 or 2.

Method 1

The reaction solution is evaporated for dryness in the vacuum and the residue is gathered in methanol. The solution is acidified with acetic acid until there is a change in colour and the solvent is distilled in the vacuum. The remaining residue is washed with water and purified by column chromatography.

Method 2

The reaction solution is withdrawn by hot aspiration and the filter residue is first washed with hot dioxane and subsequently with diethylether. The remaining residue is dissolved in methanol or water and then acidified with mineral acid until there is a clear change in colour. The solvent is distilled in the vacuum and the resulting raw product is washed with water. Subsequently column chromatography is used for purification if necessary.

Concrete examples of procedure for the substances 2a, 6e and 8a can be found in the examples 1 to 3. Other examples of these substance classes are given in the tables 2, 6 and 8.

For the substance class 3—having 2 different electrophilic groups—there is a generally valid procedure too. The procedure follows the method described under (A) but requires an equimolar proportion of a first LDA-CH-acid mixture and the 3',6'electrofuge-substituted fluoran derivative. Reprocessing is performed as described under method 1.

The resulting product is then again added to an equimolar amount of the lithium salt of a second LDA-CH-acid mixture in dioxane. This lithium salt is obtained from a second CH-acidic component and LDA. Further reprocessing is carried out according to method 1.

Example 4 shows this method using substance 3b which is typical of this substance class (cf. table 3).

Substance class 1 is reprocessed as described under (A) and the resulting intermediate product is isolated.

Subsequently, it is submitted to reaction at a high temperature (approx. 100° C.) with or without solvent, depending on the boiling point of the amine. The reaction solution is then added to ice/water and acidified with hydrochloric acid. The thus resulting product is withdrawn and purified by column chromatography.

Example 5 depicts the general procedure for the substance class 1 by illustrating the procedure for substance 1a (cf. table 1).

The compounds given for the classes 1, 2, 3, 4, 6 and 8 can for example be esterified with dicyclohexylcarbodiimide in pyridine with different alcohols. By this method the substance classes 5, 7 and 9 can for example be obtained.

EXAMPLE 1

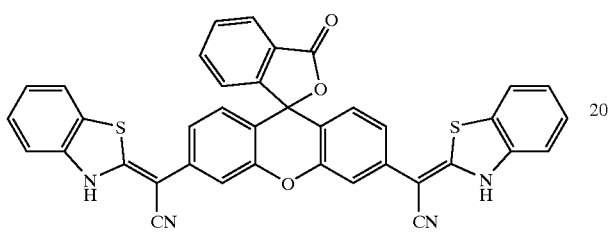

Synthesis of 3',6'-bis-(2-benzthiazolylidene-cyanomethine)-fluoran 2a

Preparation:

10.0 g 3',6'-dichlorofluoran (0.027 mol)

19.0 g 2-cyanomethylbenzthiazole [2*95 g] (0.109 mol)

11.6 ml t-butylamine [2*58 ml] (0.11 mol)

11.0 ml n-butyllithium, 10M in hexane fraction [2*55 ml] (0.110 mmol)

Procedure: method 2

Purification: the substance has already a high degree of purity

Yield: 13.6 g=0.021 mol=78% in theory

Analysis:

$C_{38}H_{20}N_4O_3S_2$ $M_G$=644.74 g/mol

Calc.: 70.79% C 3.13% H, 8.69% N.

Fnd: 70.74% C 3.23% H, 8.43% N.

Fusion point: 210° C. (Z)

$^1$H-NMR: 400 MHz LM: $CD_3OD+CH_3ONa$

| Protons | □ [ppm] (number) | Signal splitting/J [Hz] |
|---|---|---|
| H 4 | 8.01 (1) | m |
| H 5/6 | 7.57 (2) | m |
| H 7 | 7.27 (1) | m |
| H 1'/8' | 7.00 (2) | d/9.0 |
| H 2'/7 | 7.48 (2) | s (wide) |
| H 4'/5' | 8.44 (2) | s (wide) |
| H 4/7 (Bz) | 7.73/7.80 (4) | d/8.1 |
| H 5/6 (Bz) | 7.15/7.35 (4) | t/7.6 |

FT-IR (KBr): □[cm$^{-1}$]=2185 (C≡N), 1768 (C=O), 1598, 1545, 1470, 1420, 1328, 11253, 1082, 883

EI-MS: (70 eV; 280° C.) [M$^{+0}$]=644

UV/VIS:

Dianion: additive triethylamine

Cation: additive conc. sulfuric acid

| Solvent | Dianion □$_{max}$ [nm](□$_{max}$ [M$^{-1}$ cm$^{-1}$]) | Cation □$_{max}$ [nm](m$_{max}$ [M$^{-1}$ cm$^{-1}$]) |
|---|---|---|
| Methanol | 817 (125200) | 746 (87100) |
| Acetonitrile | 830 (122000) | 745 (79000) |
| Acetone | 830 (132500) | 761 (72500) |

EXAMPLE 2

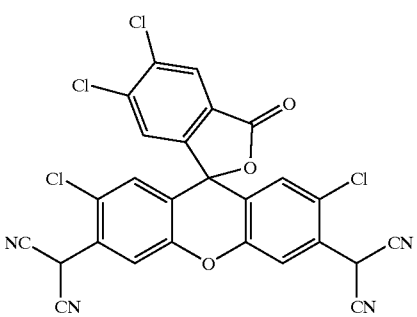

Synthesis of 5,6,2',7'-tetrachloro-3',6'-bis-(2-propyl-dinitrile)-fluoran 6e

Preparation:

3.5 g 5,6,3',6'-tetrachlorofluoran (8.00 mmol)

1.6 g malonic acid dinitrile (24.21 mmol)

2.4 ml n-butyllithium. 10M in hexane fraction (24.00 mmol)

Procedure: method 2

Purification: chromatography on silica gel (dry column) EE/PE 3:2

Yield: 2.95 g=5.21 mmol=65% d. Th.

Analysis:

$C_{26}H_8Cl_4N_4O_3$ $M_G$=566.19 g/mol

Calc.: 55.16% C, 1.42% H, 9.90% N.

$^1$H-NMR: 400 MHz LM: DMSOd$_6$

| Protons | □ [ppm] (number) | Signal splitting/J [Hz] |
|---|---|---|
| H 4 | 8.26 (1) | s |
| H 7 | 7.80 (1) | s |
| H 1'/8' | 6.88 (2) | s |
| H 4'/5' | 6.89 (2) | s |

FT-IR (KBr): ν[cm$^{-1}$]=2189 (C≡N); 1633; 1569; 1461; 1321; 1203

UV/VIS:

Dianion: additive triethylamine

Anion: additive acetic acid

| Solvent | Dianion $\lambda_{max}$ [nm]($\epsilon_{max}$ [M$^{-1}$ cm$^{-1}$]) | Anion $\lambda_{max}$ [nm]($\epsilon_{max}$ [M$^{-1}$ cm$^{-1}$]) |
| --- | --- | --- |
| Methanol | 716 (97000) | 728 (99500) |
| Acetone | 730 (74000) | 744 (93500) |

EXAMPLE 3

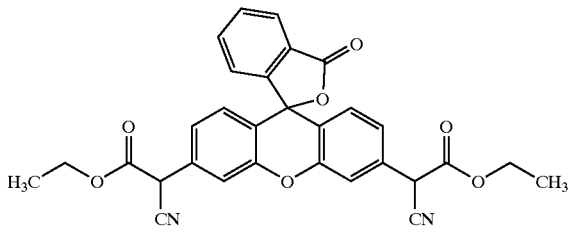

Synthesis of 3',6'-bis-(cyanoacetic acid ethyl ester-2-yl)-fluoran 8a

Preparation:

5.0 g 3',6'-dichlorofluoran (13.54 mmol)

4.1 ml cyanoacetic acid ethyl ester (38.49 mmol)

5.5 ml diisopropylamine (39.03 mmol)

3.9 ml n-butyllithium, 10M in hexane fraction (39.00 mmol)

Procedure: method 2

Purification: chromatography on silica gel (dry column) EE/PE 1:1

Yield: 4.53 g=8.67 mmol=64% d. Th.

Analysis:

$C_{30}H_{22}N_2O_7$ $M_G$=522.54 g/mol

Calc.: 68.95% C, 4.25% H, 5.36% N

Fnd: 68.51% C, 4.38% H, 5.47% N $^1$H-NMR: 400 MHz LM: CDCl$_3$

| Protons | δ [ppm] (number) | Signal splitting/J [Hz] |
| --- | --- | --- |
| H 4 | 8.06 (1) | d/8.6 |
| H 5 | 7.70 (1) | t/7.3 |
| H 6 | 7.66 (1) | t/7.3 |
| H 7 | 7.16 (1) | d/7.8 |
| H 1'/8' | 6.91 (2) | d/8.3 |
| H 2'/7' | 7.19 (2) | d/8.3 |
| H 4'/5' | 7.14 (2) | s |
| —CH—CN | 4.75 (2) | s |
| —CH$_2$— | 4.27 (4) | q/7.08 |
| —CH$_3$ | 1.31 (6) | t/7.08 |

EI-MIS: (70 eV; 260° C.) [M$^{-1}$]=522

UV/VIS: $\lambda_{max}$=695 nm; $\epsilon_{max}$=105000 M$^{-1}$ cm$^{-1}$ (Acetone. add. triethylamine) $\lambda_{max}$=676 nm; $\epsilon_{max}$=119500 M$^{-1}$ cm$^{-1}$ (Methanol. add. triethylamine)

EXAMPLE 4

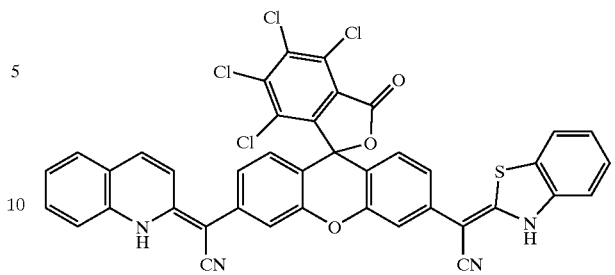

Preparation:

4.00 g 3'-(2-quinolinylide-cyanomethylene)-4,5,6,7,6'-pentachlorofluoran (6.26 mmol)

1.20 g 2-cyanomethylbenzthiazole (6.89 mmol)

0.97 ml diisopropylamine (6.86 mmol)

0.70 ml n-butyllithium in hexane fraction, 10M (7.00 mmol)

Purification: chromatography on silica gel, dry column EE/PE 1:3

Yield: 1.85 g=2.38 mmol=38% d. Th.

Analysis:

$C_{40}H_{18}Cl_4N_4O_3S$ $M_G$=776.49 g/mol

Calc: 61.87% C, 2.34% H, 7.22% N.

Fnd: 61.62% C, 2.54% H, 8.04% N.

UV/VIS: $\lambda_{max}$=859 nm; $\epsilon_{max}$=40500 M$^{-1}$ cm$^{-1}$ (methanol. additive BuOK) $\lambda_{max}$=867 nm; $\epsilon_{max}$=37500 M$^{-1}$ cm$^{-1}$ (acetonitrile, additive TEA)

EXAMPLE 5

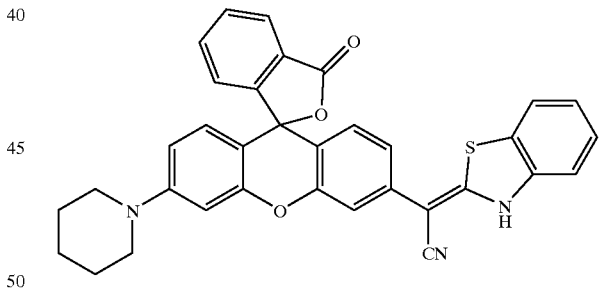

Synthesis of 3'-(2-benzthiazolylide-cyanomethylene)-6'-chlorofluoran 1a:

Preparation:

2.0 g 3'-(2-benzthiazolylide-cyanomethylene)-6'-chlorofluoran (3.95 mmol)

Purification: chromatography on silica gel (dry column) EE/PE 2:1

Yield: 1.95 g=3.51 mmol=89%

Analysis:

$C_{34}H_{25}N_3O_3S$ $M_G$=555.66 g/mol

Calc.: 73.49% C, 4.54% H, 7.56% N

Fnd: 73.03% C, 4.82% H, 7.64% N

EI-MIS: (70 eV 300° C.) [M$^-$]=555

UV/VIS:

| Solvent | Anion λmax [nm] (εmax [M⁻¹ cm⁻¹]) | Cation λmax [nm] (εmax [M⁻¹ cm⁻¹]) |
|---|---|---|
| Methanol | 723 (55000) | 624 (60500) |
| Acetonitrile | 722 (13500) | 623 (42000) |

Further examples of synthesized derivatives are given in the tables 1–9.

TABLE 1

3'-(2-benzthiazolylidene-cyanomethine)-6'-(N-piperidinyl)-fluorans

| No. | Name | Structure | Yield | λmax [nm] in MeOH |
|---|---|---|---|---|
| 1a | 3'-(2-benzthiazolylidene-cyanomethine)-6'-(N-piperidinyl)-fluoran | 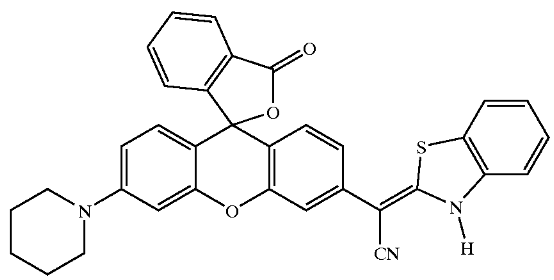 | 89% | 723 |
| 1b | 3'-(2-benzthiazolylidene-cyanomethine)-6'-(N-piperidinyl)-5,6-dichlorofluoran | 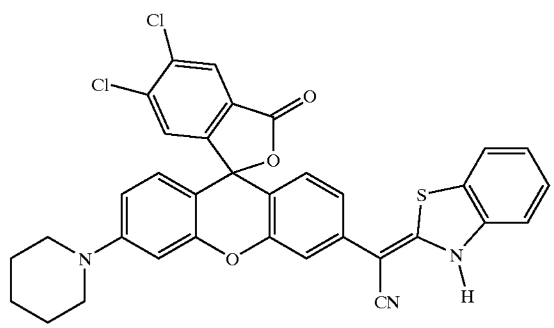 | 88% | 730 |

TABLE 2

3',6'-bis-(2-benzthiazolylidene-cyanomethine)-fluorans

| No. | Name | Structure | Yield | λmax [nm] in MeOH |
|---|---|---|---|---|
| 2a | 3',6'-bis-(2-benzthiazolyl-idene-cyanomethine)-fluoran method 2 | 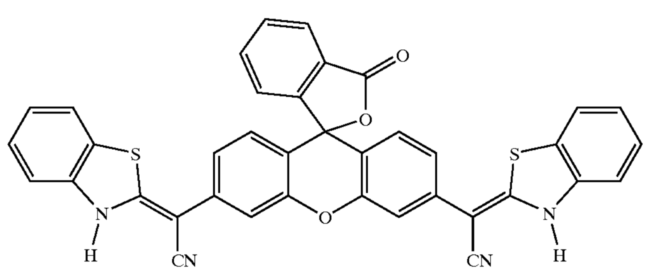 | 78% | 817 |

TABLE 2-continued

3',6'-bis-(2-benzthiazolylidene-cyanomethine)-fluorans

| No. | Name | Structure | Yield | $\lambda_{max}$ [nm] in MeOH |
|---|---|---|---|---|
| 2b | 3',6'-bis-(2-benzthiazolyl-idene-cyanomethine)-5(6)-carboxyfluoran method 2 | 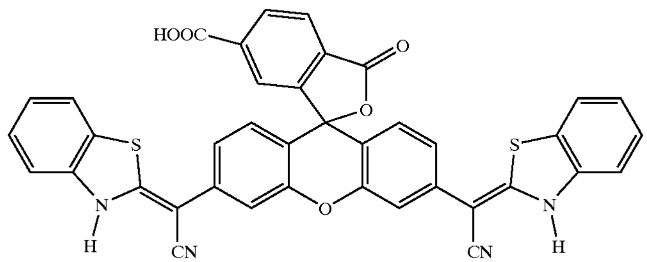 | 69% | 819 |
| 2c | 3',6'-bis-(2-benzthiazolyl-idene-cyanomethine)-5(6)-sulfofluoran method 2 | 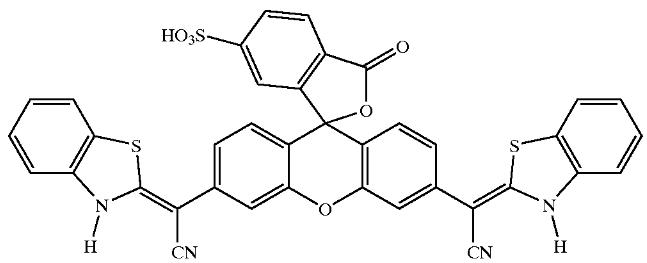 | 65% | 825 |
| 2d | 3',6'-bis-(2-benzthiazolyl-idene-cyanomethine)-4',5'-dibromofluoran method 1 | 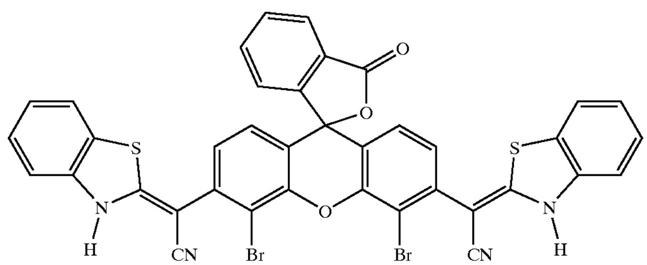 | 49% | 845 |
| 2e | 3',6'-bis-(2-benzthiazolyl-idene-cyanomethine)-5,6-dichlorofluoran method 2 | 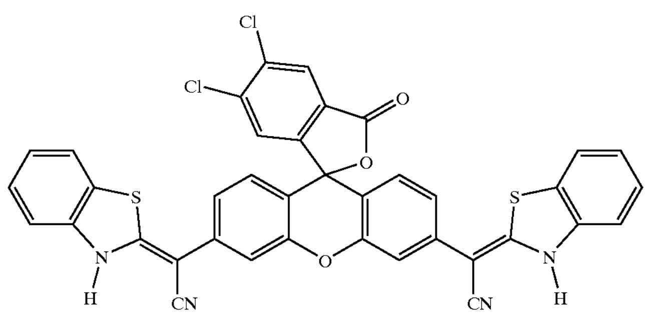 | 73% | 834 |
| 2f | 3',6'-bis-(2-benzthiazolyl-idene-cyanomethine)-4,5,6,7-tetrachlorofluoran method 2 | 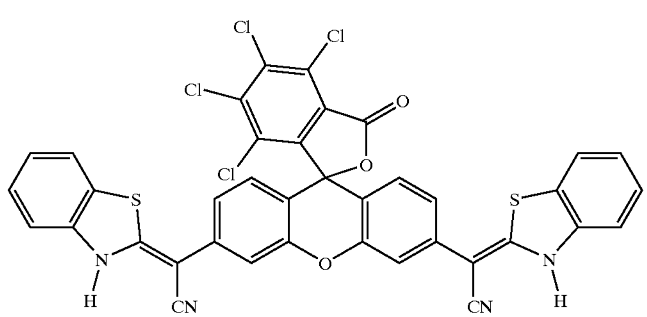 | 67% | 876 |

TABLE 2-continued

3',6'-bis-(2-benzthiazolylidene-cyanomethine)-fluorans

| No. | Name | Structure | Yield | $\lambda_{max}$ [nm] in MeOH |
|---|---|---|---|---|
| 2g | 3',6'-bis-(2-benzthiazolyl-idene-cyanomethine)-2',7'-dichlorofluoran<br>method 1 | 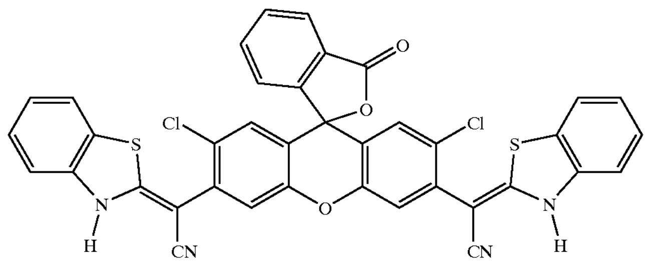 | 44% | 860 |
| 2h | 3',6'-bis-(2-benzthiazolyl-idene-cyanomethine)-4,5,2',7'-tetrachlorofluoran<br>method 2 | 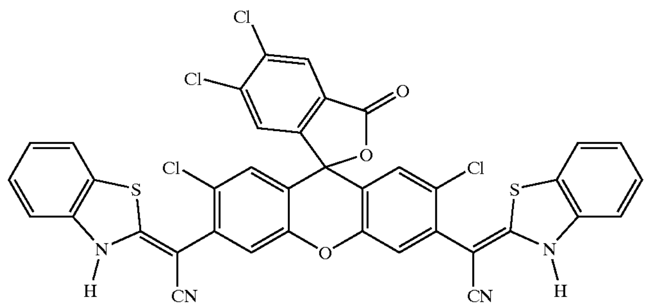 | 86% | 874 |
| 2i | 3',6'-bis-(2-benzthiazolyl-idene-cyanomethine)-3,4,5,6,2',7'-hexachloro-fluoran<br>method 2 | 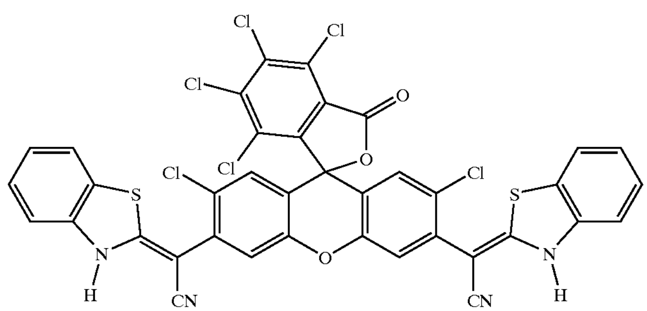 | 56% | 914 |
| 2j | 3',6'-bis-(2-benzthiazolyl-idene-cyanomethine)-4',5'-dimethylfluoran<br>method 1 | 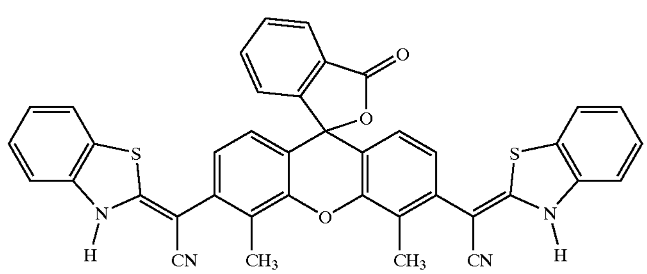 | 71% | 859 |
| 2k | 3',6'-bis-(2-benzthiazolyl-idene-cyanomethine)-5,6-dichloro-4',5'-dimethyl-fluoran<br>method 1 | 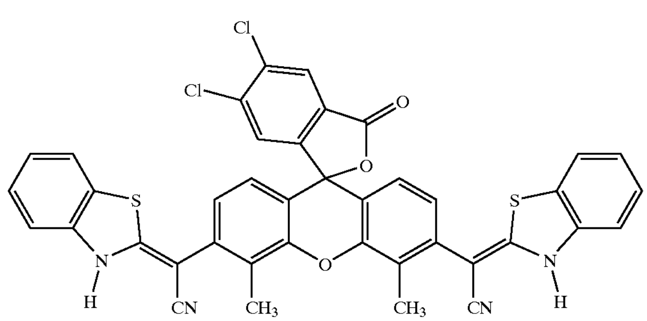 | 55% | 865 |

TABLE 2-continued

3',6'-bis-(2-benzthiazolylidene-cyanomethine)-fluorans

| No. | Name | Structure | Yield | $\lambda_{max}$ [nm] in MeOH |
|---|---|---|---|---|
| 2l | 3',6'-bis-(2-benzthiazolyl-idene-cyanomethine)-4,5,6,7-tetrachloro-4',5'-dimethylfluoran method 1 | 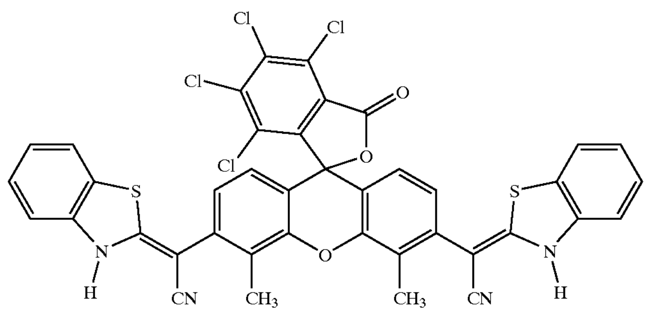 | 57% | 890 |
| 2m | 3',6'-bis-(2-benzthiazolyl-idene-cyanomethine)-2',7'-dihexylfluoran method 1 | 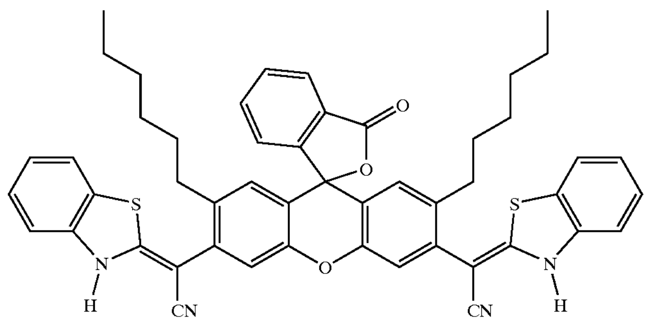 | 52% | 839 |
| 2n | 3',6'-bis-(2-benzthiazolyl-idene-cyanomethine)-5(6)-carboxy-2',7'-dihexylfluoran method 1 | 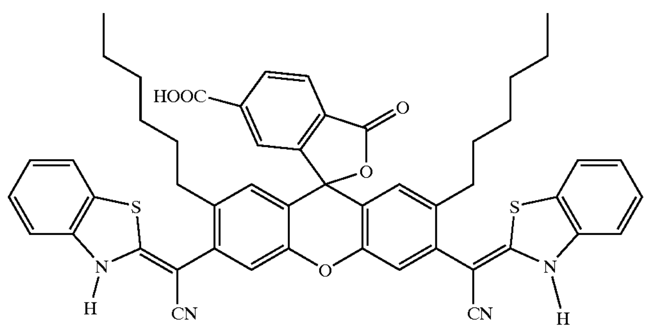 | 35% | 842 |
| 2o | 3',6'-bis-(2-benzthiazolyl-idene-cyanomethine)-5,6-dichloro-2',7'-dihexyl-fluoran method 1 | 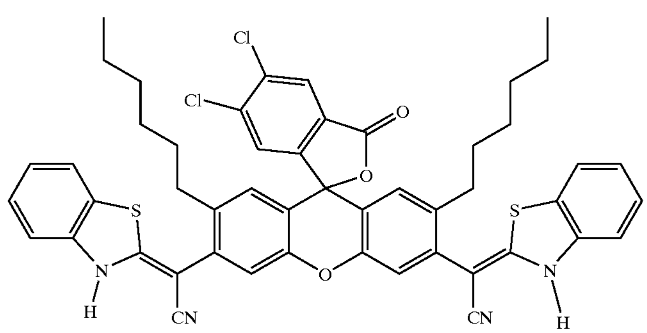 | 66% | 856 |

TABLE 2-continued

3',6'-bis-(2-benzthiazolylidene-cyanomethine)-fluorans

| No. | Name | Structure | Yield | $\lambda_{max}$ [nm] in MeOH |
|---|---|---|---|---|
| 2p | 3',6'-bis-(2-benzthiazolyl-idene-cyanomethine)-4,5,6,7-tetrachloro-2',7'-dihexylfluoran method 1 | 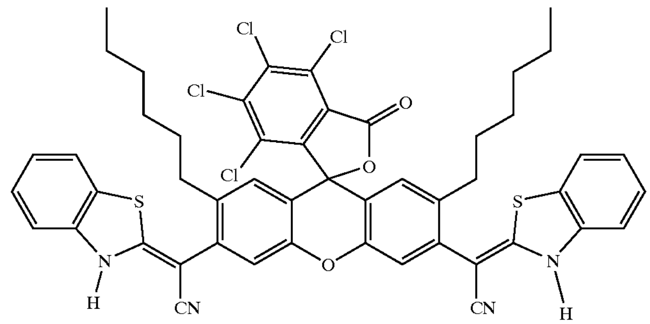 | 78% | 882 |

TABLE 3

3'-(2-Benzthiazolylidene-cyanomethine)-6'-(2-quinolinylidene-cyanomethine)-fluorans

| No. | Name | Structure | Yield | $\lambda_{max}$ [nm] in MeOH |
|---|---|---|---|---|
| 3a | 3'-(2-Benzthiazolyl-idene-cyanomethine)-6'-(2-quinolinylidene-cyano-methine)-5,6-dichloro-fluoran | 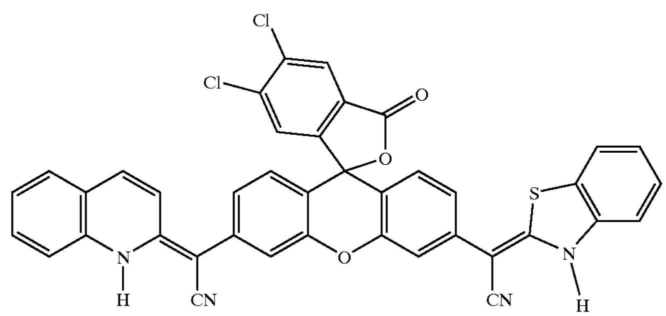 | 42% | 843 |
| 3b | 3'-(2-benzthiazolyl-idene-cyanomethine)-6'-(2-quinolinylidene-cyano-methine)-4,5,6,7-tetra-chlorofluoran | 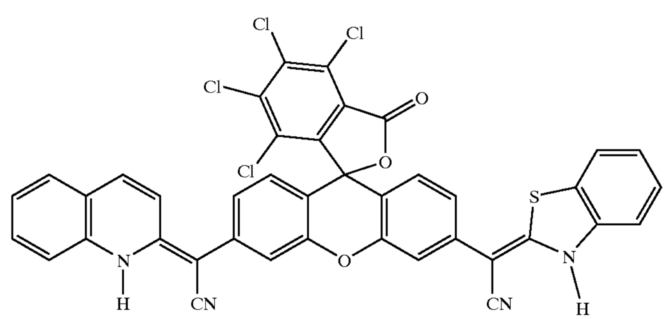 | 38% | 859 |
| 3c | 3'-(2-benzthiazolyl-idene-cyanomethine)-6'-(2-quinolinylidene-cyano-methine)-5,6,2',7'-tetra-chlorofluoran | 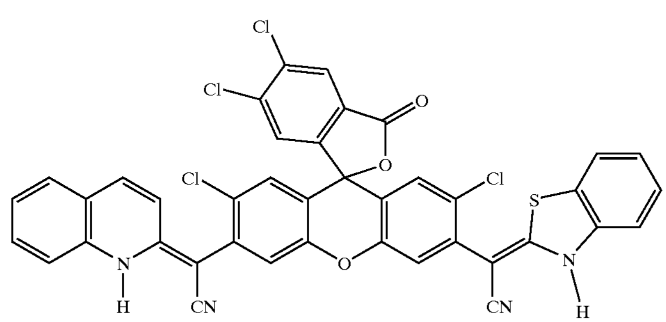 | 41% | 880 |

TABLE 3-continued

3'-(2-Benzthiazolylidene-cyanomethine)-6'-(2-quinolinylidene-cyanomethine)-fluorans

| No. | Name | Structure | Yield | $\lambda_{max}$ [nm] in MeOH |
|---|---|---|---|---|
| 3d | 3'-(2-benzthiazolyl-idene-cyanomethine)-6'-(2-quinolinylidene-cyanomethine)-4',5'-dimethyl-fluoran | 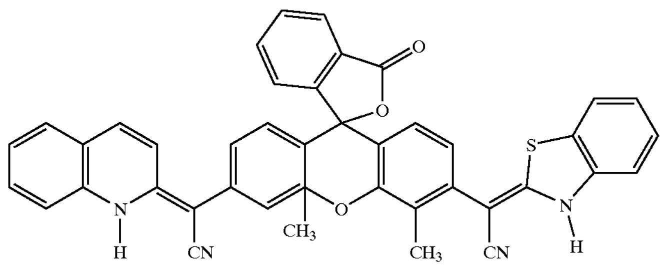 | 45% | 835 |
| 3e | 3'-(2-benzthiazolyl-idene-cyanomethine)-6'-(2-quinolinylidene-cyanomethine)-5,6-dichloro-4',5'-dimethylfluoran | 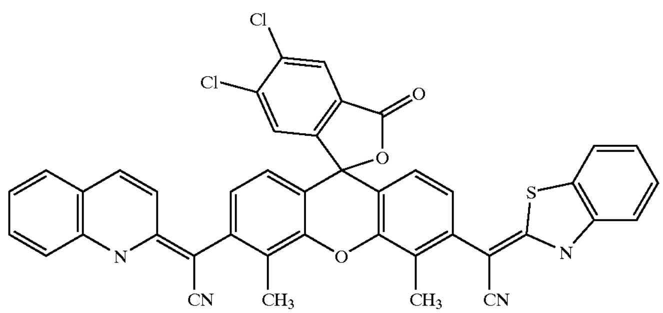 | 35% | 848 |
| 3f | 3'-(2-benzthiazolyl-idene-cyanomethine)-6'-(2-quinolinylidene-cyanomethine)-4,5,6,7-tetrachloro-4',5'-dimethyl-fluoran | 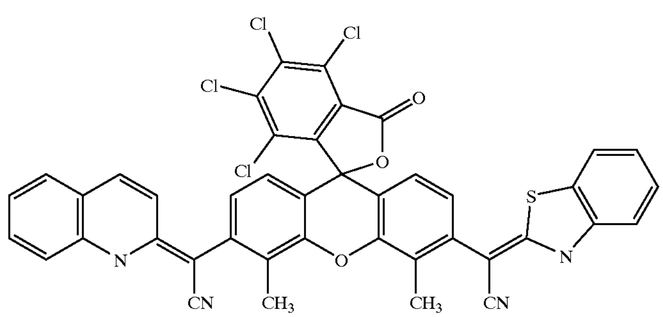 | 28% | 860 |
| 3g | 3'-(2-benzthiazolyl-idene-cyanomethine)-6'-(2-quinolinylidene-cyanomethine)-4,5,6,7-tetrachloro-2',7'-dihexyl-fluoran | 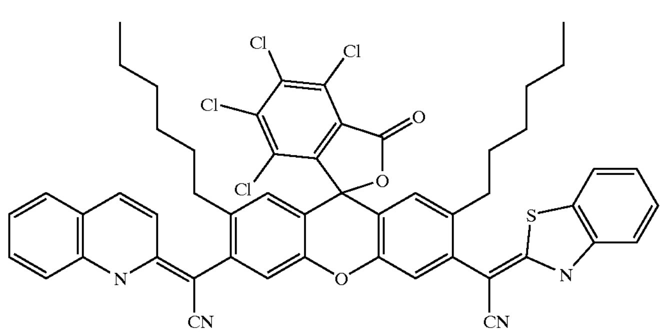 | 25% | 886 |

TABLE 4

3',6'-bis-(4-quinolinylidene-cyanomethine)-fluorans

| No. | Name | Structure | Yield | $\lambda_{max}$ [nm] in MeOH |
|---|---|---|---|---|
| 4a | 3',6'-bis-(4-quinolinylidene-cyanomethine)-fluoran method 1 | 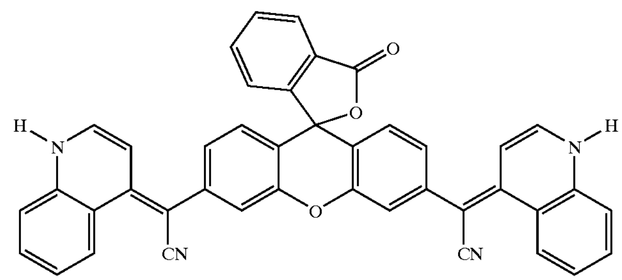 | 39% | 795 |
| 4b | 3',6'-bis-(4-quinolinylidene-cyanomethine)-5,6-2',7'-tetrachlorofluoran method 1 | 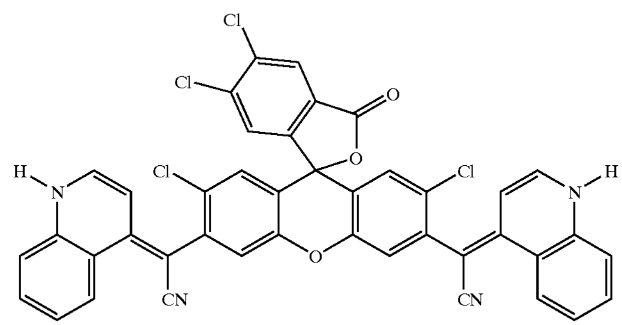 | 32% | 874 |
| 4c | 3',6'-bis-(4-quinolinylidene-cyanomethine)-4,5,6,7-tetrachloro-2',7'-dihexylfluoran method 1 | 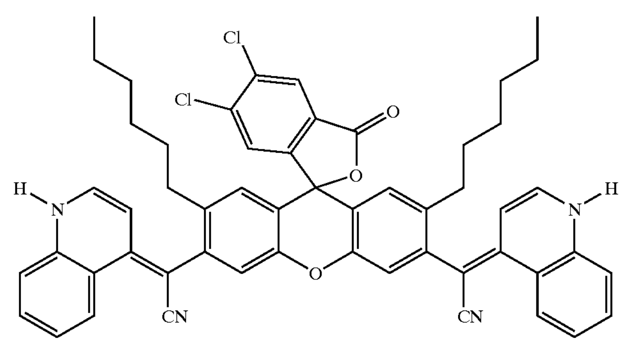 | 32% | 802 |

TABLE 5

3-(2-benzthiazolyl-cyanomethine)-6-(2-benzthiazolylidene-cyanomethine)-9-(2-phenylcarboxylic acid ester)-xanthene-3-ylidene

| No. | Name | Structure | Yield | $\lambda_{max}$ [nm] in MeOH |
|---|---|---|---|---|
| 5a | 3-(2-benzthiazolyl-cyanomethine)-6-(2-benzthiazolylidene-cyanomethine)-9-(2-phenylcarboxylic acid benzyl ester)-xanthene-3-ylidene | 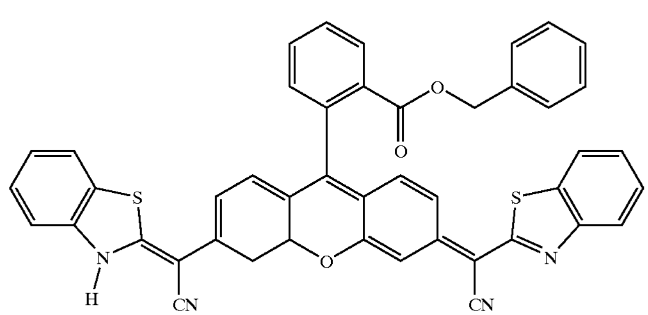 | 64% | 838 |

TABLE 5-continued 3-(2-benzthiazolyl-cyanomethine)-6-(2-benzthiazolylidene-cyanomethine)-9-(2-phenylcarboxylic acid ester)-xanthene-3-ylidene

| No. | Name | Structure | Yield | $\lambda_{max}$ [nm] in MeOH |
|---|---|---|---|---|
| 5b | 3-(2-benzthiazolyl-cyanomethine)-6-(2-benzthiazolylidene-cyanomethine)-9-[2-phenylcarboxylic acid-(2-chloroethyl)ester]-xanthene-3-ylidene | 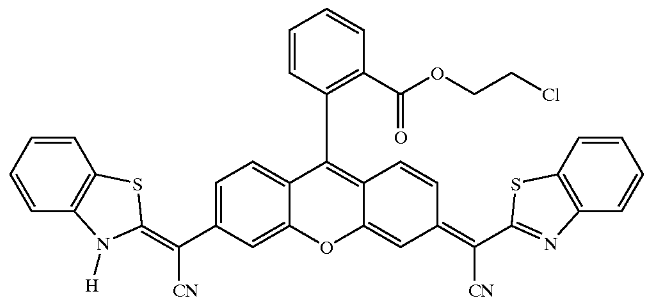 | 59% | 840 |
| 5c | 3-(2-benzthiazolyl-cyanomethine)-6-(2-benzthiazolylidene-cyanomethine)-9-(2-phenylcarboxylic acid ethyl ester)-xanthene-3-ylidene | 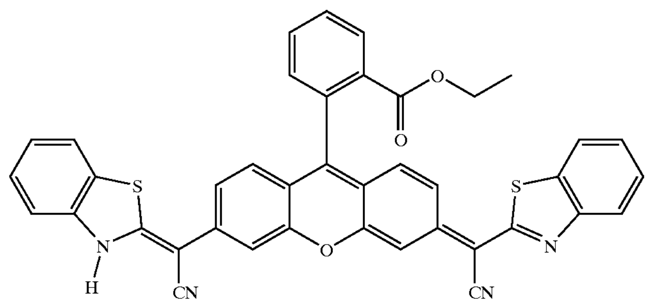 | 73% | 840 |
| 5d | 3-(2-benzthiazolyl-cyanomethine)-6-(2-benzthiazolylidene-cyanomethine)-9-(2-phenylcarboxylic acid myristyl ester)-xanthene-3-ylidene | 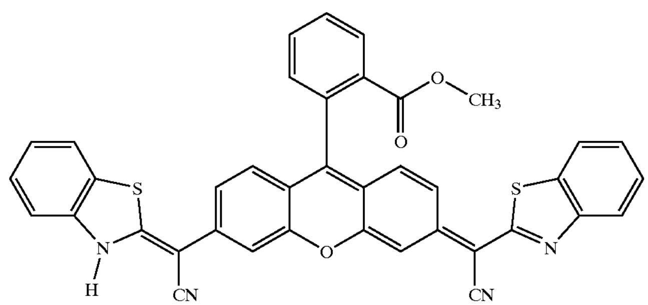 | 58% | 840 |
| 5e | 3-(2-benzthiazolyl-cyanomethine)-6-(2-benzthiazolylidene-cyanomethine)-9-[2-phenylcarboxylic acid-(N-hydroxy-succinimidyl)-ester]-xanthene-3-ylidene | 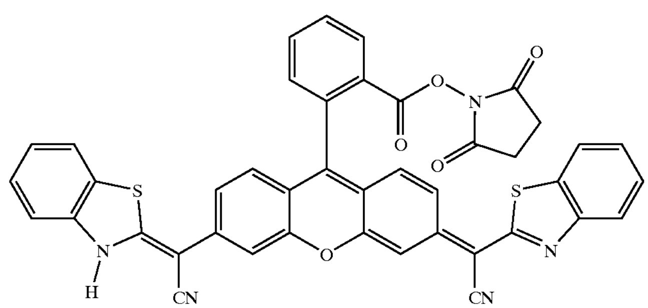 | 62% | 831 |
| 5f | 3-(2-benzthiazolyl-cyanomethine)-6-(2-benzthiazolylidene-cyanomethine)-9-[2-phenylcarboxylic acid (2-triethyleneglycol ester)]-xanthene-3-ylidene | 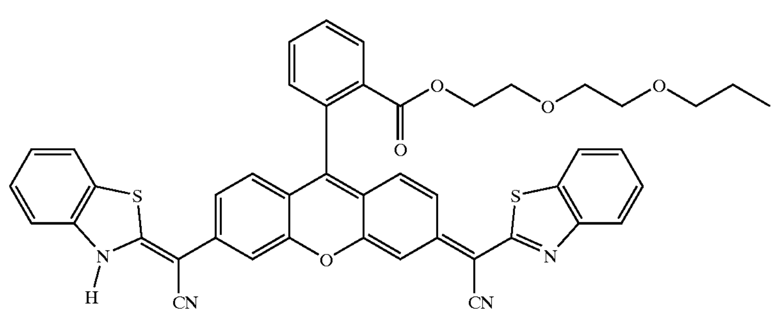 | 58% | 840 |

TABLE 5-continued 3-(2-benzthiazolyl-cyanomethine)-6-(2-benzthiazolylidene-cyanomethine)-9-(2-phenylcarboxylic acid ester)-xanthene-3-ylidene

| No. | Name | Structure | Yield | λmax [nm] in MeOH |
|---|---|---|---|---|
| 5g | 3-(2-benzthiazolyl-cyanomethine)-6-(2-benzthiazolylidene-cyanomethine)-9-{phenyl-2,4(5)-bis-[carboxylic acid-(N-hydroxysuccinimidyl)-ester]}-xanthene-3-ylidene | 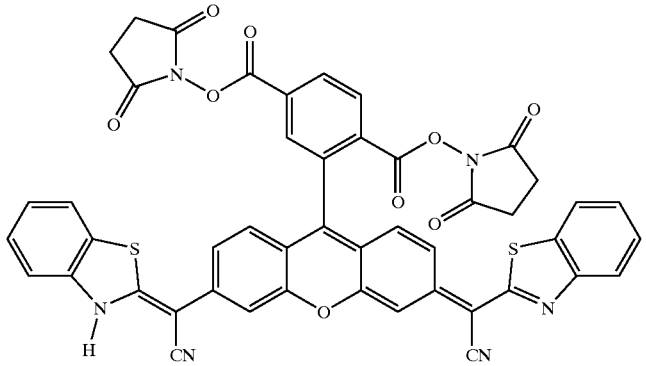 | 51% | 833 |
| 5h | 3-(2-benzthiazolyl-cyanomethine)-6-(2-benzthiazolylidene-cyanomethine)-9-(3,4,5,6-tetrachloro-phenyl-2-carboxylic acid-ethyl ester)-xanthene-3-ylidene | 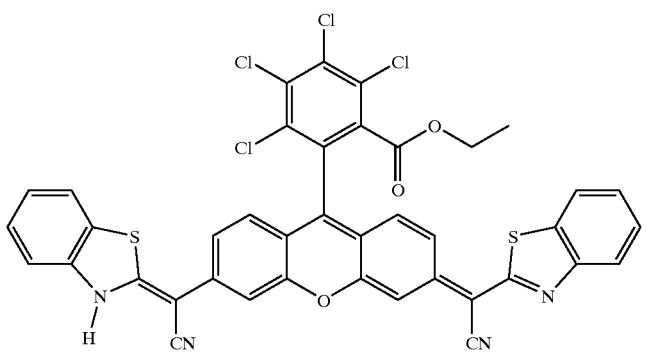 | 48% | 880 |
| 5i | 3-(2-benzthiazolyl-cyanomethine)-6-(2-benzthiazolylidene-cyanomethine)-9-(2-phenylcarboxylic acid-morpholinamide)-xanthene-3-ylidene | 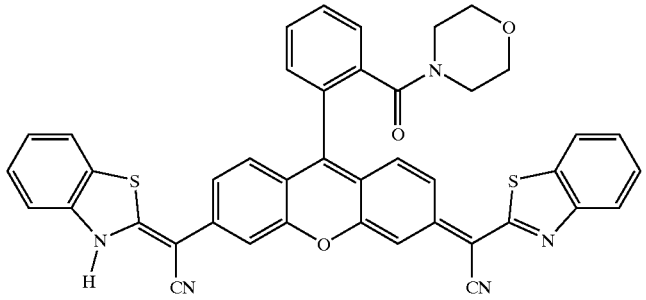 | 64% | 852 |

TABLE 6

3',6'-bis-(2-propyldinitril)-fluorans

| No. | Name | Structure | Yield | λmax [nm] in MeOH |
|---|---|---|---|---|
| 6a | 3',6'-bis-(2-propyldinitril)-fluoran method 2 | 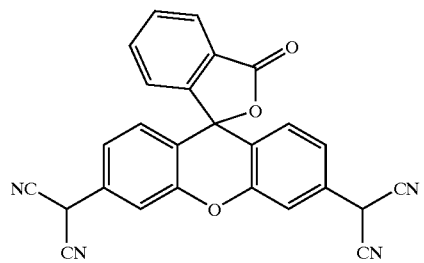 | 56% | 673 |

TABLE 6-continued

3',6'-bis-(2-propyldinitril)-fluorans

| No. | Name | Structure | Yield | λmax [nm] in MeOH |
|---|---|---|---|---|
| 6b | 5(6)-carboxy-3',6'-bis-(2-propyldinitril)-fluoran method 2 | 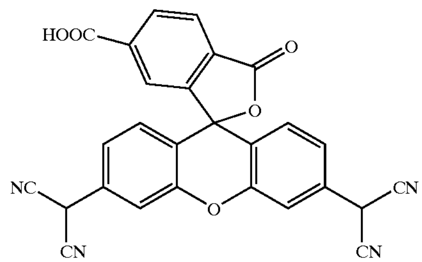 | 60% | 675 |
| 6c | 5,6-dichloro-3',6'-bis-(2-propyldinitril)-fluoran method 2 | 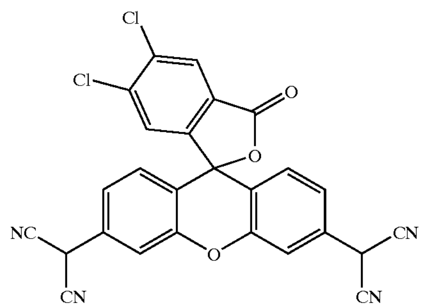 | 58% | 683 |
| 6d | 4,5,6,7-tetrachloro-3',6'-bis-(2-propyldinitril)-fluoran method 2 | 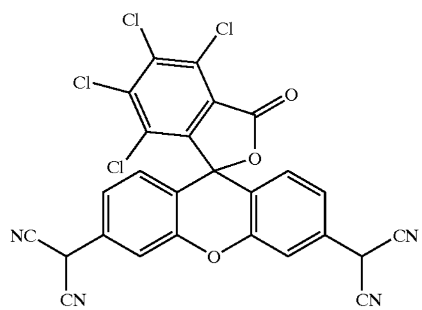 | 16% | 710 |
| 6e | 5,6,2',7'-tetrachloro-3',6'-bis-(2-propyldinitril)-fluoran method 2 | 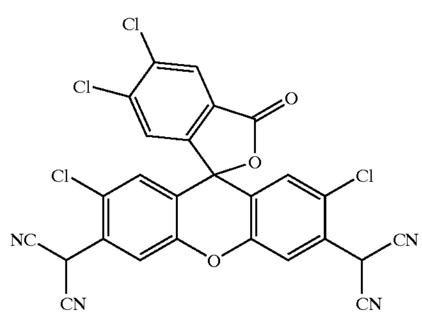 | 67% | 716 |
| 6f | 5,6-dichloro-4',5'-dimethyl-3',6'-bis-(2-propyldinitril)-fluoran method 2 | 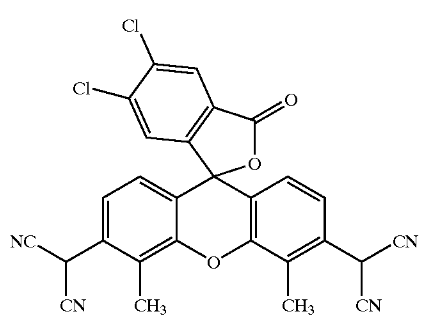 | 61% | 690 |

TABLE 6-continued

3',6'-bis-(2-propyldinitril)-fluorans

| No. | Name | Structure | Yield | $\lambda_{max}$ [nm] in MeOH |
|---|---|---|---|---|
| 6g | 5(6)carboxy-2',7'-dichloro-3',6'-bis-(2-propyldinitril)-fluoran<br>method 2 | 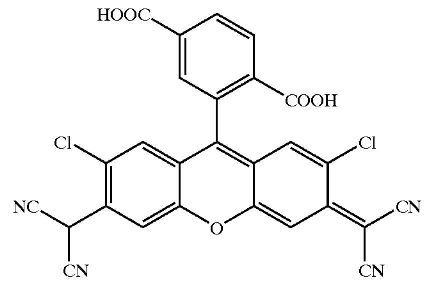 | 30% | 700 |

TABLE 7

2,7-Dichloro-3,6-bis-(2-propyldinitril)-9-(2,4(5)-phenyldicarboxylic acid-di-(N-hydroxysuccinimidyl ester)-xanthene-3-ylidene

| No. | Name | Structure | Yield | $\lambda_{max}$ [nm] in MeOH |
|---|---|---|---|---|
| 7 | 2,7-dichloro-3,6-bis-(2-propyldinitril)-9-(2,4(5)-phenyl-dicarboxylic acid-di-(N-hydroxysuccinimidyl ester)-xanthene-3-ylidene | 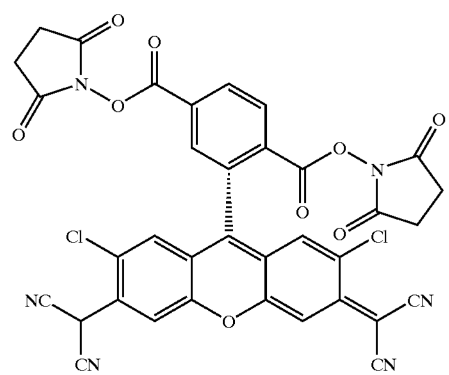 | 15% | 708 |

TABLE 8

3',6'-bis-(cyanoacetic acid ethyl ester-2-yl)-fluorans

| No. | Name | Structure | Yield | $\lambda_{max}$ [nm] in MeOH |
|---|---|---|---|---|
| 8a | 3',6'-bis-(cyanoacetic acid ethyl ester-2-yl)-fluoran<br>method 2 | 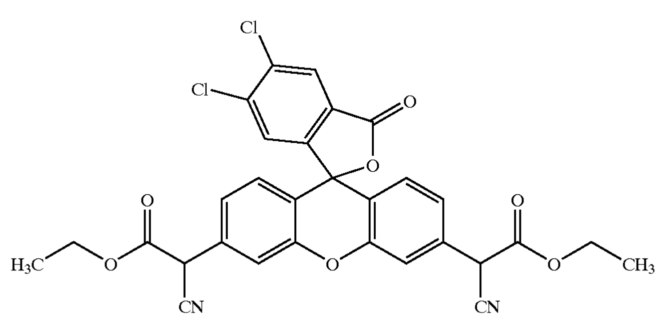 | 64% | 676 |

TABLE 8-continued

3',6'-bis-(cyanoacetic acid ethyl ester-2-yl)-fluorans

| No. | Name | Structure | Yield | $\lambda_{max}$ [nm] in MeOH |
|---|---|---|---|---|
| 8b | 5(6)-carboxy-3',6'-bis-(cyanoacetic acid ethyl ester-2-yl)-fluoran method 2 | 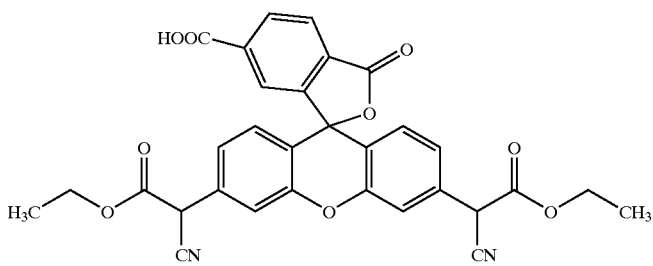 | 62% | 678 |
| 8c | 5,6-dichloro-3',6'-bis-(cyanoacetic acid ethyl ester-2-yl)-fluoran method 2 | 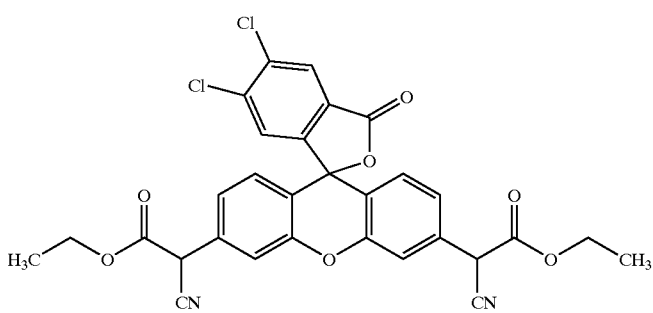 | 62% | 680 |

TABLE 9

3,6-bis-(cyanoacetic acid ethyl ester-2-yl)-9-(2-phenylcarboxylic acid ethyl ester)-xanthene-3-ylidenes

| Nr. | Name | Structure | Yield | $\lambda_{max}$ [nm] in acetone |
|---|---|---|---|---|
| 9a | 3,6-bis-(cyanoacetic acid ethyl ester-2-yl)-9-(2-phenylcarboxylic acid ethyl ester)-xanthane-3-ylidene | 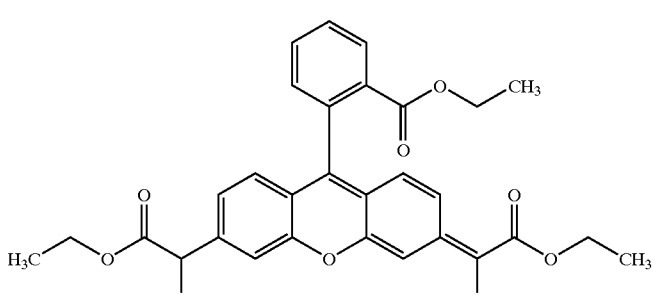 | 60% | 695 |
| 9b | 3,6-bis-(cyanoacetic acid ethyl ester-2-yl)-9-[2-phenyl-carboxylic acid-(N-hydroxysuccinimidyl) ester]-xanthene-3-ylidene | 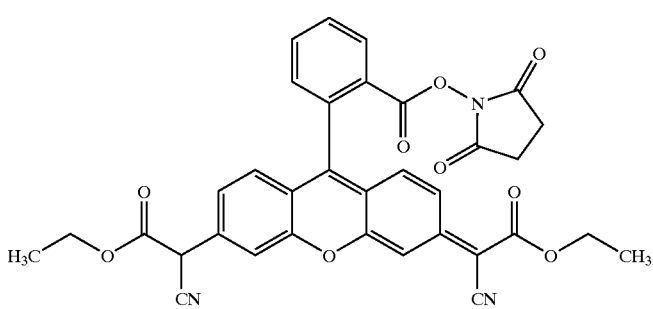 | 62% | 689 |

TABLE 9-continued 3,6-bis-(cyanoacetic acid ethyl ester-2-yl)-9-(2-phenylcarboxylic acid ethyl ester)-xanthene-3-ylidenes

| Nr. | Name | Structure | Yield | $\lambda_{max}$ [nm] in acetone |
|---|---|---|---|---|
| 9c | 3,6-bis-(cyanoacetic acid ethyl ester-2-yl)-9-(2,4(5)-phenyl-dicarboxylic acid-diethyl ester)-xanthene-3-ylidene | 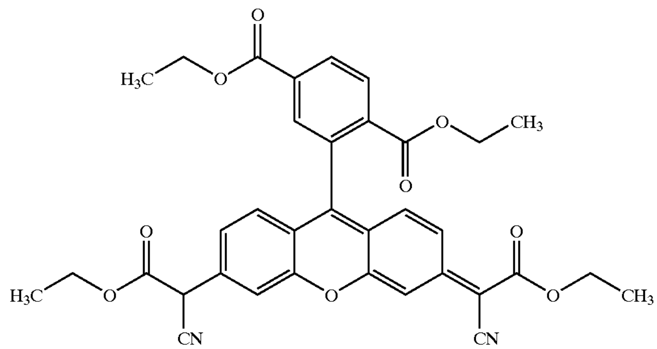 | 60% | 701 |
| 9d | 3,6-bis-(cyanoacetic acid ethyl ester-2-yl)-9-(4,5-dichloro-2-phenyl-carboxylic acid-ethyl ester)-xanthene-3-ylidene | 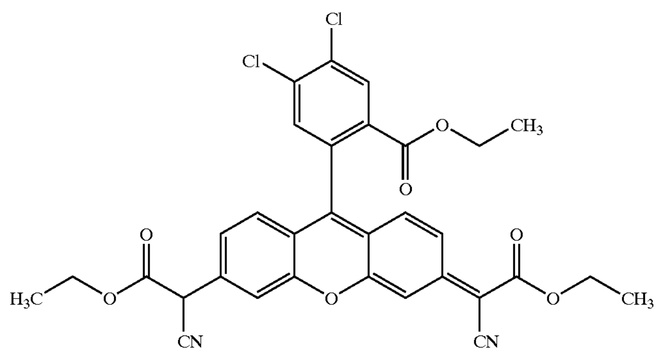 | 54% | 720 |
| 9e | 3,6-bis-(cyanoacetic acid ethyl ester-2-yl)-9-[4,5-dichloro-2-phenyl-carboxylic acid-(N-hydroxysuccinimidyl) ester]-xanthene-3-ylidene | 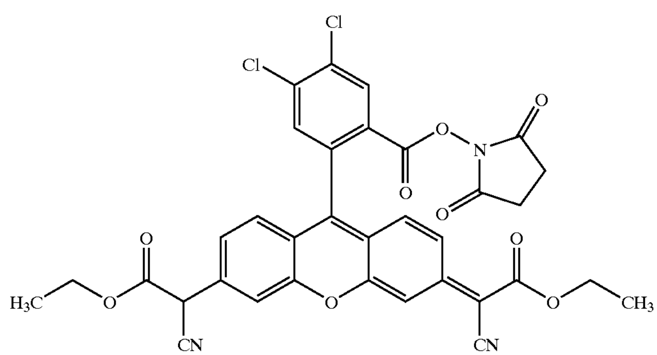 | 64% | 731 |
| 9f | 3,6-bis-(cyanoacetic acid ethyl ester-2-yl)-9-(2,4(5)-phenyl-dicarboxylic acid-di-(N-hydroxysuccinimidyl ester)-xanthene-3-ylidene | 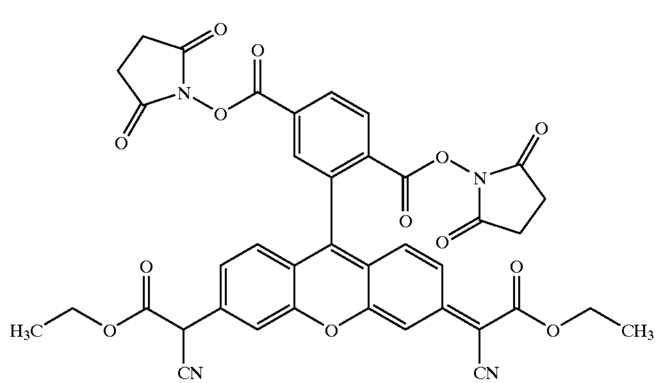 | 20% | 698 |

What is claimed is:

1. A compound of the formula:

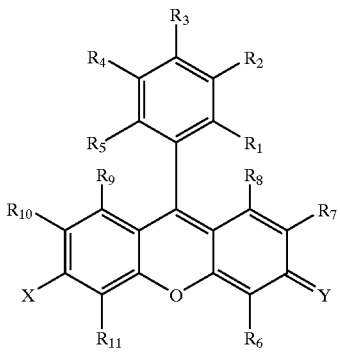

wherein R1, R2, R3, R4 and R5 are selected from the group consisting of hydrogen, alkyl, aryl, heteroaryl, alkoxy, cyano, hydroxy, halogen, isocyanate, isothiocyanate, carboxylic acid, sulfonic acid, and derivatives of carboxylic acid or sulfonic acid selected from the group consisting of alkoxycarbonyl, aryloxycarbonyl, N-hydroxysuccinimide esters, acid halogenides, unsubstituted amino and substituted amino selected from the group consisting of ω-amino alcohols, ω-aminocarboxylic acids and ω-aminohalogen alkanes, with the proviso that at least one of R1, R2, R3, R4 and R5 is a carboxylic acid or derivative thereof, R6, R7, R8, R9, R10 and R11 are selected from the group consisting of hydrogen, alkyl, substituted alkyl, and halogen, and X is selected from the group consisting of amines, substituted amines, heteroarylidenecyanomethine residues, and malonic acid derivatives selected from the group consisting of 2-propyldinitril residues and cyanoacetic acid esters; Y is selected from the group consisting of heteroarylidenecyanomethine residues, and malonic acid derivatives selected from the group consisting of 2-propyldinitril residues and cyanoacetic acid esters.

2. The compound of claim 1, wherein said heteroarylidenecyanomethine residues are selected from the group consisting of 2-benzthiazolylidenecyanomethine and 2- or 4-quinolinylidenecyanomethine.

3. The compound of claim 1, wherein X and Y are identical.

4. The compound of claim 1, wherein X and Y are different.

5. The compound 3',6'-bis-(2-benzthiazolylidene-cyanomethine)-fluoran.

6. The compound 5,6,2',7'-tetrachloro-3',6'-bis-(2-propyldinitrile)-fluoran.

7. The compound 3',6'-bis-(cyanoacetic acid ethyl ester-2-yl)-fluoran.

8. The compound 3'-(2-benzthiazolylidene-cyanomethine)-3'-(2-quinolinylidene-cyanomethine)-4,5,6,7-tetrachlorofluoran.

9. The compound 3'-(2-benzthiazolylidene-cyanomethylene)-6'-chlorofluoran.

10. The compound 3',6'-bis-(2-benzthiazolylidene-cyanomethine)-5(6)-carboxyfluoran.

11. The compound 3',6'-bis-(2-benzthiazolylidene-cyanomethine)-5(6)-sulfofluoran.

12. The compound 3-(2-benzthiazolyl-cyanomethine)-6-(2-benzthiazolylidene-cyanomethine)-9-[2-phenylcarboxylic acid-(2-chloroethyl)-ester]-xanthene-3-ylidene.

13. The compound 3-(2-benzthiazolyl-cyanomethine)-6-(2-benzthiazolylidene-cyanomethine)-9-[2-phenylcarboxylic acid-(N-hydroxysuccinimidyl)-ester]-xanthene-3-ylidene.

14. The compound 3-(2-benzthiazolyl-cyanomethine)-6-(2-benzthiazolylidene-cyanomethine)-9-{phenyl-2,4,(5)-bis[carboxylic acid-(N-hydroxysuccinimidyl)-ester]}-xanthene3-ylidene.

15. The compound 5(6)-carboxy-3',6'-bis-(2-propyldinitril)-fluoran.

16. The compound 2,7-dichloro-3,6-bis-(2-propyldinitril)-9-(2,4(5)-phenyl-dicarboxylic acid-di-(N-hydroxysuccinimidyl ester)-xanthene-3-ylidene.

17. The compound 3,6bis-(cyanoacetic acid ethyl ester-2-yl)-9-[2-phenyl-carboxylic acid-(N-hydroxysuccinimidyl)-ester]-xanthene-3-ylidene.

18. The compound 3,6-bis-(cyanoacetic acid ethyl ester-2-yl)-9-[4,5-dichloro-2-phenyl-carboxylic acid-N-hydroxysuccinimidyl)ester]-xanthene-3-ylidene.

19. The compound 3,6-bis-(cyanoacetic acid ethyl ester-2-yl)-9-(2,4(5)-phenyl-dicarboxylic acid-di-(N-hydroxysuccinimidyl ester)-xanthene-3-ylidene.

* * * * *